United States Patent
Adams et al.

(10) Patent No.: US 8,734,394 B2
(45) Date of Patent: May 27, 2014

(54) AUTOMATIC INJECTION DEVICE WITH DELAY MECHANISM INCLUDING DUAL FUNCTIONING BIASING MEMBER

(75) Inventors: Matthew Robert Adams, Mountain View, CA (US); Jesse Arnold Fourt, Mountain View, CA (US); Jonathan I. Kaplan, Palo Alto, CA (US); Paul Joseph Silberschatz, San Francisco, CA (US); James R. Yurchenco, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/581,057

(22) PCT Filed: Feb. 24, 2011

(86) PCT No.: PCT/US2011/025988
§ 371 (c)(1),
(2), (4) Date: Aug. 24, 2012

(87) PCT Pub. No.: WO2011/109205
PCT Pub. Date: Sep. 9, 2011

(65) Prior Publication Data
US 2012/0323177 A1 Dec. 20, 2012

Related U.S. Application Data

(60) Provisional application No. 61/309,186, filed on Mar. 1, 2010.

(51) Int. Cl.
*A61M 5/315* (2006.01)
*A61M 5/20* (2006.01)

(52) U.S. Cl.
USPC .......................... 604/135; 604/228; 604/242

(58) Field of Classification Search
USPC ......... 604/107, 110, 157, 208, 210, 242, 135, 604/228
See application file for complete search history.

(56) References Cited

U.S. PATENT DOCUMENTS 2,752,918 A 7/1956 Uytenbogaart
4,561,856 A 12/1985 Cochran
(Continued)

FOREIGN PATENT DOCUMENTS

EP 0470977 2/1992
EP 0653220 5/1995
(Continued)

*Primary Examiner* — Quynh-Nhu H Vu
(74) *Attorney, Agent, or Firm* — Edward J. Prein

(57) ABSTRACT

An automatic injection apparatus including a delay mechanism for properly delivering medication prior to the needled syringe of the apparatus being retracted. In one form, the delay mechanism includes a shuttle (170) for the syringe, a follower (250), a locking member, a damping compound between the follower and a supporting surface (308) to dampen rotation of the follower relative to the shuttle, and a dual functioning biasing member (290) acting between the shuttle and the follower. When the locking member moves to a release position during an injection, the dual functioning biasing member first provides a torsional force to force the follower to rotate relative to the shuttle from a latching position to an unlatching position, and then the dual functioning biasing member provides an axial force to force the shuttle axially relative to the follower to move the shuttle for retracting the syringe needle into the housing of the apparatus after injection.

8 Claims, 18 Drawing Sheets

(56) References Cited

U.S. PATENT DOCUMENTS

| | | |
|---|---|---|
| 4,744,786 A | 5/1988 | Hooven |
| 5,080,649 A | 1/1992 | Vetter |
| 5,150,933 A | 9/1992 | Myslicki et al. |
| 5,167,304 A | 12/1992 | Capek |
| 5,300,030 A | 4/1994 | Crossman et al. |
| 5,346,480 A | 9/1994 | Hess et al. |
| 5,393,301 A | 2/1995 | Goldberg |
| 5,514,097 A | 5/1996 | Knauer |
| 5,540,664 A | 7/1996 | Wyrick |
| 5,779,677 A | 7/1998 | Frezza |
| 6,077,247 A | 6/2000 | Marshall et al. |
| 6,159,181 A | 12/2000 | Crossman et al. |
| 6,221,046 B1 | 4/2001 | Burroughs et al. |
| 6,258,068 B1 | 7/2001 | Kirchhofer et al. |
| 6,387,078 B1 | 5/2002 | Gillespie, III |
| 6,454,743 B1 | 9/2002 | Weber |
| 6,475,194 B2 | 11/2002 | Domici, Jr. et al. |
| 6,544,234 B1 | 4/2003 | Gabriel |
| 6,589,210 B1 | 7/2003 | Rolfe |
| 6,632,198 B2 | 10/2003 | Caizza |
| 7,066,907 B2 | 6/2006 | Crossman et al. |
| 7,097,634 B2 | 8/2006 | Gilbert |
| 7,361,160 B2 | 4/2008 | Hommann et al. |
| 7,465,289 B2 | 12/2008 | Marshall |
| 7,563,252 B2 | 7/2009 | Marshall et al. |
| 7,635,356 B2 | 12/2009 | Stamp |
| 7,699,816 B2 | 4/2010 | Kirchhofer et al. |
| 7,758,548 B2 | 7/2010 | Gillespie et al. |
| 7,901,377 B1 | 3/2011 | Harrison et al. |
| 8,048,029 B2 | 11/2011 | Gillespie et al. |
| 8,052,653 B2 | 11/2011 | Gratwohl et al. |
| 8,167,840 B2 | 5/2012 | Matusch |
| 2003/0105430 A1 | 6/2003 | Lavi et al. |
| 2004/0024367 A1 | 2/2004 | Gilbert |
| 2006/0184132 A1 | 8/2006 | Watson |
| 2006/0258990 A1 | 11/2006 | Weber |
| 2007/0021720 A1 | 1/2007 | Guillermo |
| 2007/0173770 A1 | 7/2007 | Stamp |
| 2009/0012470 A1 | 1/2009 | Barrow-Williams |
| 2010/0049125 A1* | 2/2010 | James et al. .................. 604/110 |
| 2010/0069845 A1 | 3/2010 | Marshall et al. |
| 2010/0160894 A1* | 6/2010 | Julian et al. .................. 604/506 |
| 2011/0034878 A1* | 2/2011 | Radmer et al. ............... 604/192 |
| 2013/0123697 A1 | 5/2013 | Ekman et al. |

FOREIGN PATENT DOCUMENTS

| | | |
|---|---|---|
| EP | 0678303 | 10/1995 |
| EP | 0996473 | 5/2000 |
| ES | 2070782 | 6/1995 |
| GB | 728248 | 4/1955 |
| GB | 2388033 | 11/2003 |
| GB | 2396298 | 6/2004 |
| GB | 2396816 | 7/2004 |
| GB | 2397767 | 8/2004 |
| GB | 2463034 | 3/2010 |
| WO | 9903529 | 1/1999 |
| WO | 00/24441 | 5/2000 |
| WO | 03/092771 | 11/2003 |
| WO | 03/097133 | 11/2003 |
| WO | 2004/054645 | 7/2004 |
| WO | 2005/115508 | 12/2005 |
| WO | 2005/115512 | 12/2005 |
| WO | 2005/115514 | 12/2005 |
| WO | 2005/115516 | 12/2005 |
| WO | 2006/106291 | 10/2006 |
| WO | 2006/106295 | 10/2006 |
| WO | 2007/002052 | 1/2007 |
| WO | 2007/002053 | 1/2007 |
| WO | 2007/036676 | 4/2007 |
| WO | 2008/112472 | 9/2008 |
| WO | 2009/092807 | 7/2009 |

* cited by examiner

AUTOMATIC INJECTION DEVICE WITH DELAY MECHANISM INCLUDING DUAL FUNCTIONING BIASING MEMBER

BACKGROUND OF THE INVENTION

The present invention pertains to pharmaceutical injection devices, and, in particular, to an automatic injection device.

Patients suffering from a number of different diseases frequently must inject themselves with pharmaceuticals. A variety of devices have been proposed to facilitate these injections. One type of device is an automatic injection device. This type of device, when triggered by a user, automatically inserts into the user a needle of a syringe that prior to triggering was disposed within the device housing, and then automatically injects a dose of medication through that inserted needle. One known type of automatic injection device then automatically advances a shroud to cover the needle when the dose is completed. In another type of automatic injection device having a configuration more desirable to some, and instead of having an advancing shroud, the device will automatically retract the needle into the housing when the dose is completed. One difficulty with designing an automatic injector with a needle retracting feature is ensuring both that the full desired contents of the syringe have been injected and that the syringe needle is properly retracted into the device housing after use.

International Publication Number WO 2005/115516 explains in additional detail such design difficulty, and further proposes solutions using a type of delay mechanism involving a highly viscous fluid damping. While perhaps functional, these solutions are not without their own shortcomings, such as the delay mechanism being used to transfer force to the syringe during injection.

International Publication Number WO 2008/112472 discloses an automatic injector with delay mechanism which has desirable capabilities but which is of larger diameter than may be desirable for some. Further, the number of parts, and the camming motion of the delay mechanism with parts sliding against each other, complicates assembly and operation.

Automatic injectors frequently are provided with a lock feature that frustrates device triggering prior to a user having prepared for such triggering. One known way of triggering an automatic injector is for a manually operable button to unlatch prongs of a spring-loaded plunging element of the device, such as by the splaying outward or squeezing inward of such prongs to allow passage of the prongs through one or more openings in the surface to which the prongs releasably latch. Various means to prevent this plunger unlatching from occurring too soon have been employed in the past, but such means are not without their shortcomings, such as due to increasing the device complexity or adding undesirable size to the device.

Thus, it would be desirable to provide an automatic injection apparatus that can overcome one or more of these and other shortcomings of the prior art.

BRIEF SUMMARY OF THE INVENTION

In one form thereof, the present invention provides a delay mechanism for an automatic injection apparatus having a housing, a needled syringe with a plunger, and at least one biasing element for moving the needled syringe in a first direction within the housing to extend the needle of the syringe beyond the housing and to advance the plunger to force syringe contents through the needle for an injection. The delay mechanism includes a shuttle for the syringe, the shuttle including a first latching element; a follower including a second latching element, the second latching element for cooperating with the first latching element to limit motion of the shuttle relative to the follower in a second direction opposite the first direction; a locking member movable within the housing from a locking position to a release position by engagement with the syringe plunger during an injection, the locking member, when in the locking position, preventing rotation of the follower relative to the shuttle, the locking member, when in the release position, allowing rotation of the follower relative to the shuttle; a damping compound between the follower and a supporting surface to dampen rotation of the follower relative to the shuttle; and a dual functioning biasing member acting between the shuttle and the follower, the biasing member providing both a torsional force urging the follower to rotate relative to the shuttle and an axial force urging the shuttle away from the follower; whereby when the locking member moves to the release position during an injection, the dual functioning biasing member first forces the follower to rotate relative to the shuttle from a latching position, at which the first and second latching elements cooperate, to an unlatching position, at which the second latching element is disengaged from the first latching element, and then the dual functioning biasing member forces the shuttle axially relative to the follower to move the shuttle for retracting the syringe needle into the housing after injection.

One advantage of the present invention is that a delay mechanism may be provided for an automatic injection which allows a timely retraction of the needle without a release from or overcoming of the driving spring of the syringe, and which is not substantially involved with operational forces applied to the syringe during needle insertion and then injection.

Another advantage of the present invention is that an automatic injection device may be provided with a slim profile.

Another advantage of the present invention is that an automatic injection device, and such as a delay mechanism therein, may be provided using a reduced number of parts while still having a reliable staging of device operation.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
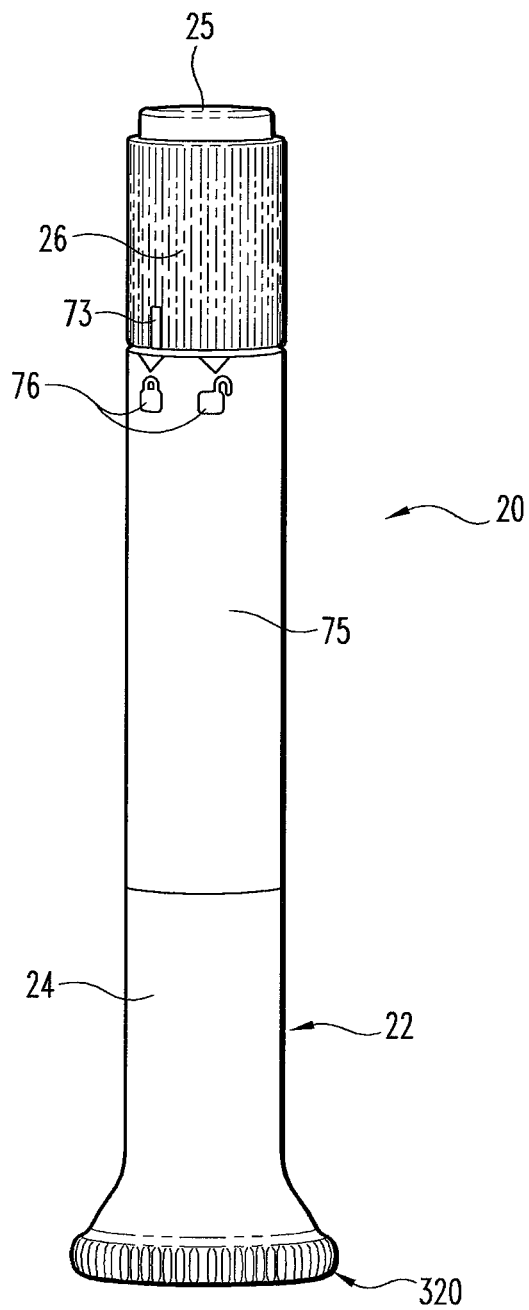
FIG. 1 is a side view of an automatic injection apparatus with delay mechanism of the present invention.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 2:
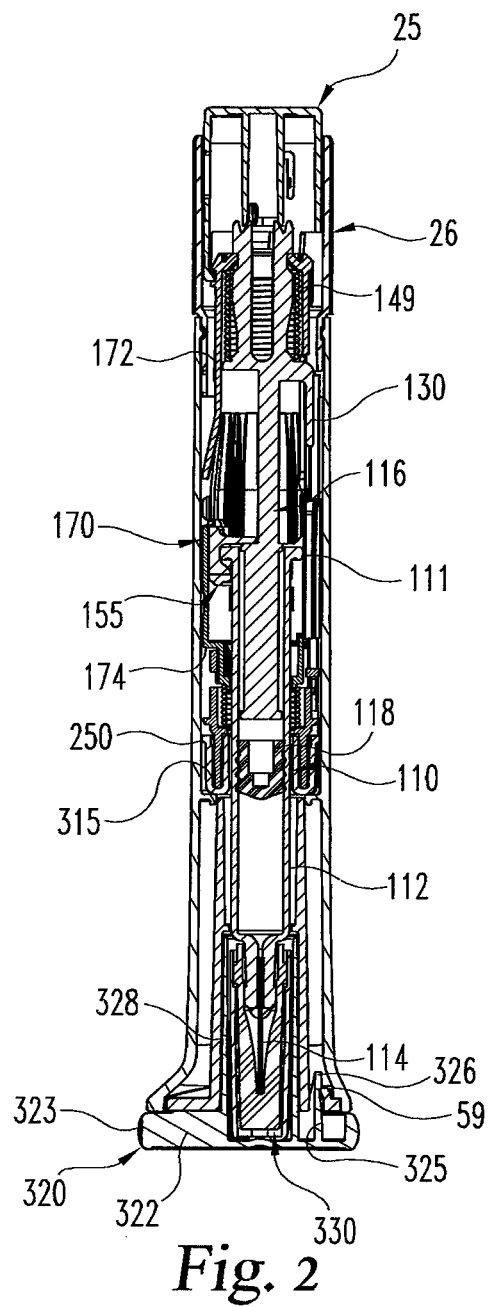
FIG. 2 is a longitudinal cross-sectional view of the automatic injection apparatus of FIG. 1.

Referring now to FIGS. 1 and 2, there are shown different views of a first embodiment of an automatic injection apparatus with a delay mechanism of the present invention.

The automatic injection apparatus, generally designated 20, has a trigger that when actuated by a user results in the needled syringe of the apparatus automatically being driven downward such that the injection needle projects beyond the bottom end of the apparatus housing to penetrate the user. The apparatus then proceeds to inject automatically the medication contents of the syringe through the needle, after which the syringe is retracted automatically such that the injection needle is returned to within the housing. The delay mechanism of the apparatus helps to stage the operation to ensure that the medication contents are properly delivered prior to the needled syringe being retracted.

It will be appreciated from the following description that apparatus 20 is conceptually similar in various aspects to the devices disclosed in International Publication Number WO 2008/112472, which publication is incorporated herein in its entirety.

Apparatus 20 includes an outer housing 22 in which are operationally disposed working components of the apparatus. At the top or distal end of the housing and protruding axially therefrom, a safety-controlled button 25 that is part of the user-operated trigger is provided. When the safety sleeve 26 of the housing is disposed in a proper angular orientation relative to the housing body 24 as rotatably adjusted by the user, button 25 is unlocked and can be depressed to start the automatic injection function of the apparatus. As used herein, distal and proximal refer to axial locations relative to an injection site when the apparatus is oriented for use at such site, whereby, for example, proximal end of the housing refers to the housing end that is closest to such injection site.

Figure 3A:
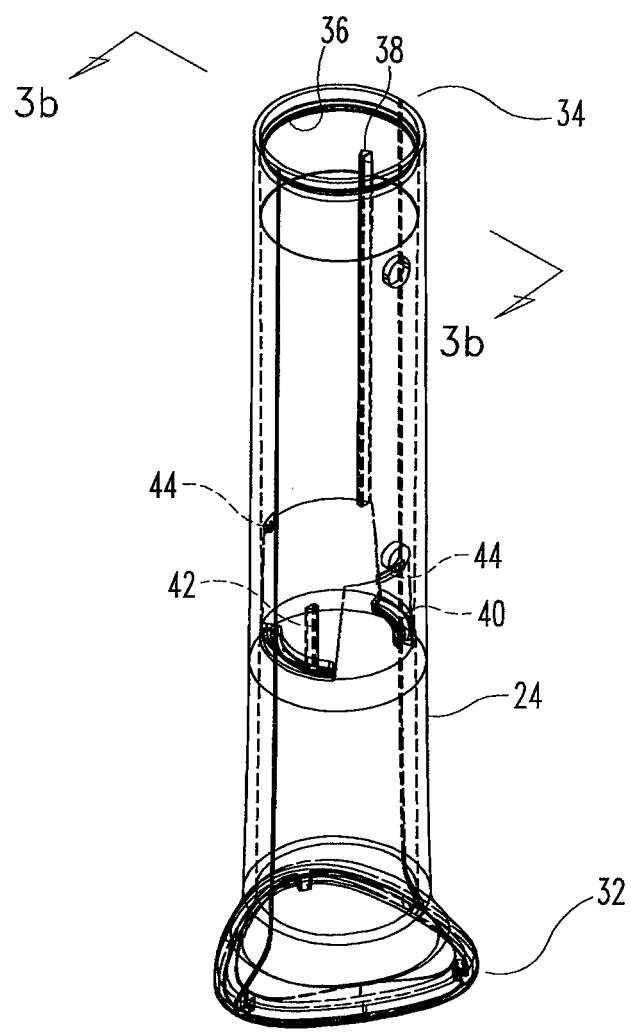
FIGS. 3a and 3b are respectively perspective and longitudinal cross-sectional views of a main housing body of the apparatus of FIG. 1 shown separate from the other apparatus components.
Figure 3B:
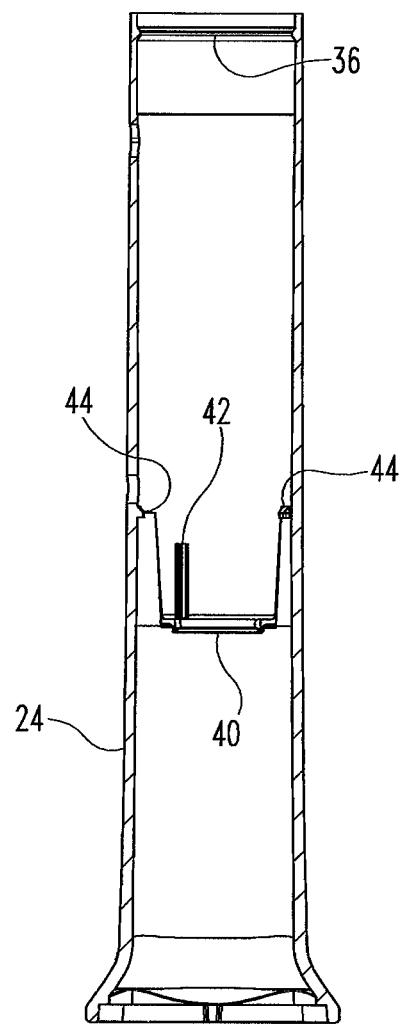

As further shown in FIGS. 3a and 3b, a tubular main body 24 of housing 22 extends between a proximal end 32 and a distal end 34 and is formed from a transparent plastic material, such as ABS plastic. Near the main body distal end, a circumferential or annular snap ring 36 projects inwardly from the housing body interior surface. A longitudinally extending rib 38 for guiding the syringe shuttle projects from the body interior surface proximally of snap ring 36. Near a middle length portion of body 24, a pair of angularly spaced ledges or ribs 40 is formed on the body interior surface for supporting the grease or damping collar 300. An axially extending spline 42 formed on the housing interior surface above one of the ledges 40 serves to rotatably fix collar 300 within the housing. A set of circumferentially spaced retention snaps or ribs 44 angularly offset from ledges 40 and located distally thereof serve to axially locate the follower 250.

Figure 4A:
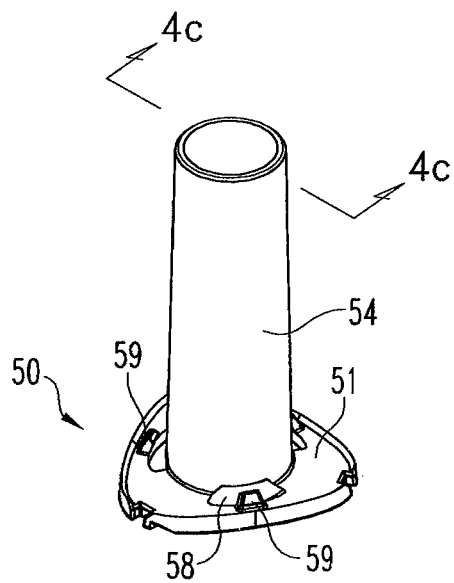
FIGS. 4a, 4b and 4c are respectively perspective, bottom perspective, and longitudinal cross-sectional views of a housing baseplate of the apparatus of FIG. 1 shown separate from the other apparatus components.
Figure 4B:
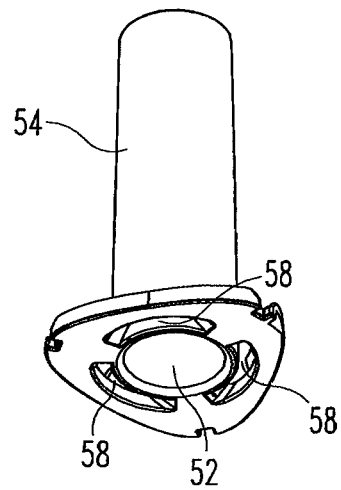
Figure 4C:
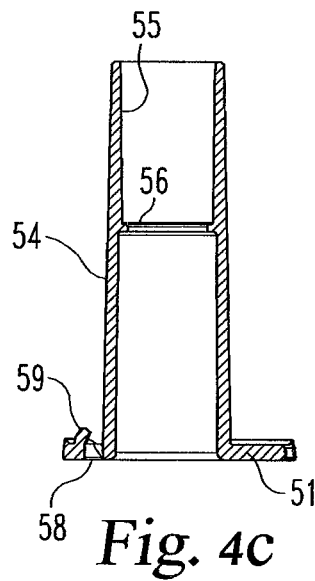
Figure 5A:
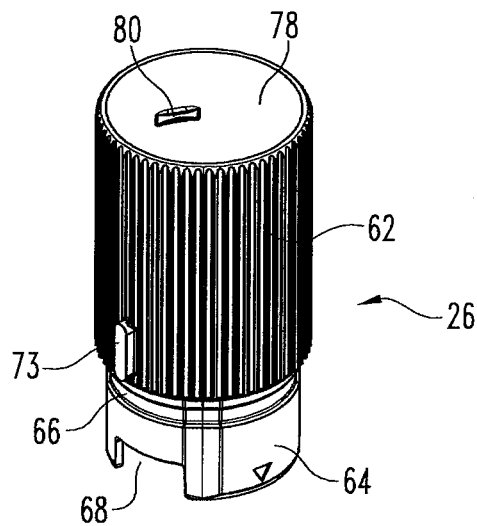
FIGS. 5a, 5b, 5c and 5d are respectively perspective, bottom perspective, top and longitudinal cross-sectional views of a housing safety sleeve of the apparatus of FIG. 1 shown separate from the other apparatus components.
Figure 5B:
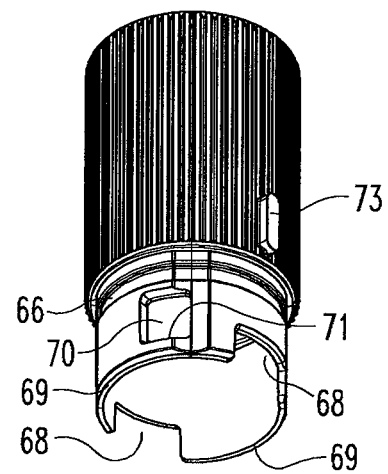
Figure 5C:
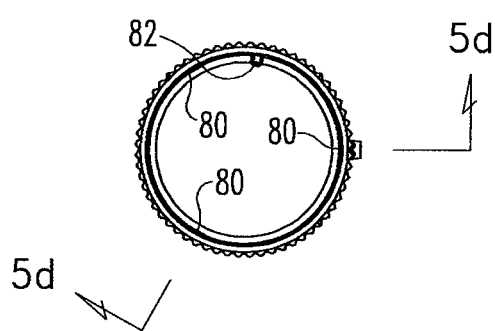
Figure 5D:
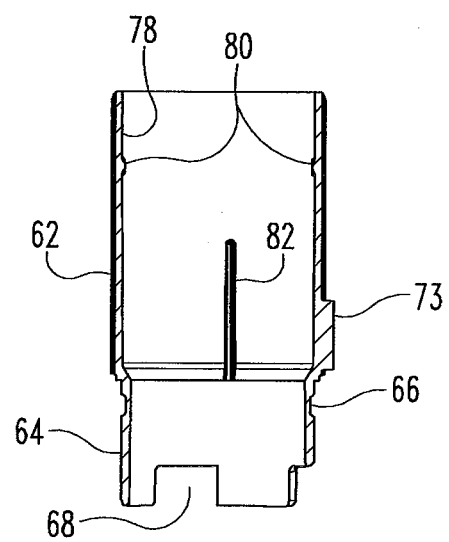
Figure 6A:
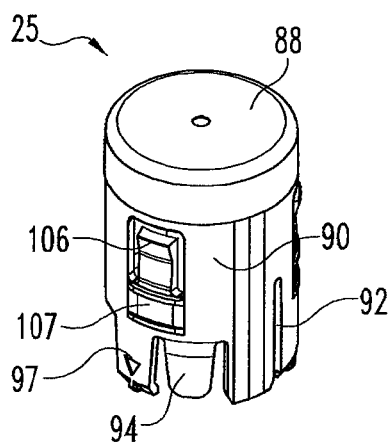
FIGS. 6a, 6b, 6c, 6d and 6e are respectively perspective, side, first longitudinal cross-sectional, bottom perspective and second longitudinal cross-sectional views of a button shown separate from the other apparatus components.
Figure 6B:
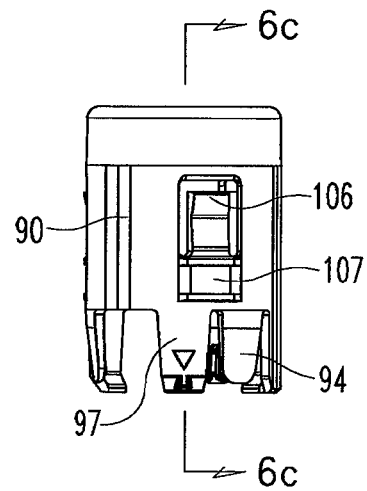
Figure 6C:
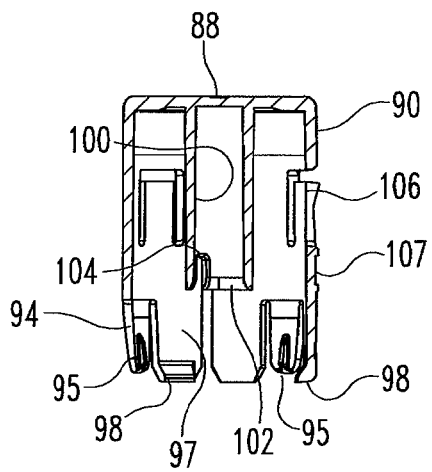
Figure 6D:
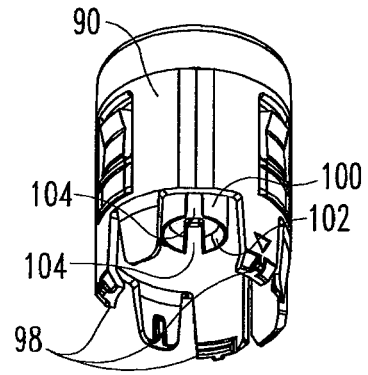
Figure 6E:
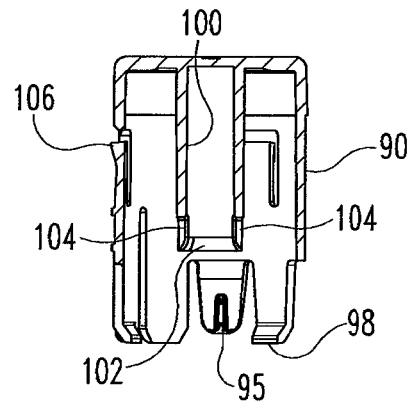
Figure 7A:
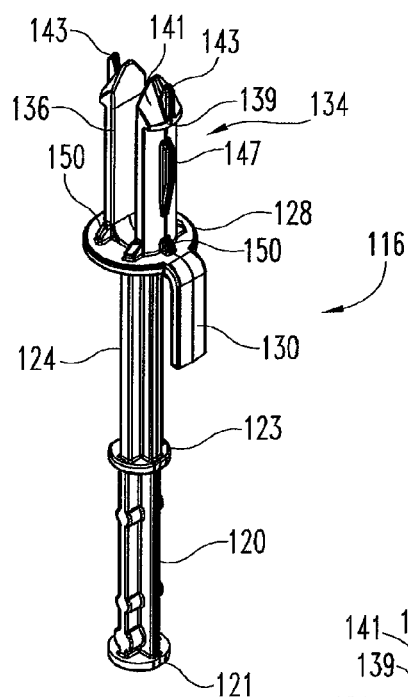
FIGS. 7a, 7b, 7c, and 7d are respectively two perspective, side and top views of a plunger element shown separate from the other apparatus components.
Figure 7B:
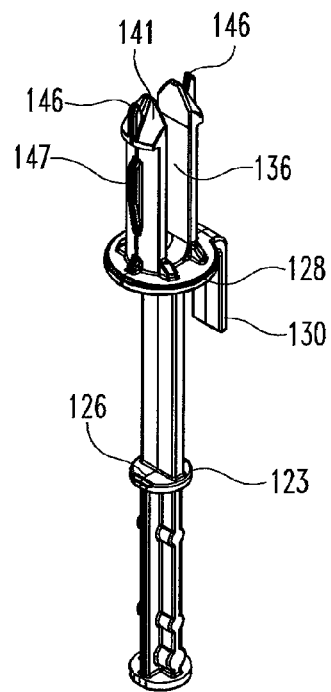
Figure 7C:
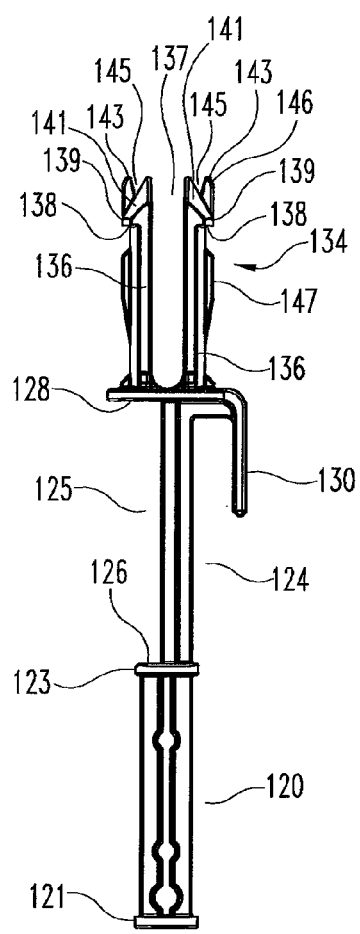
Figure 7D:
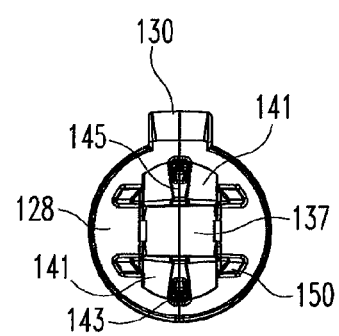
Figure 8A:
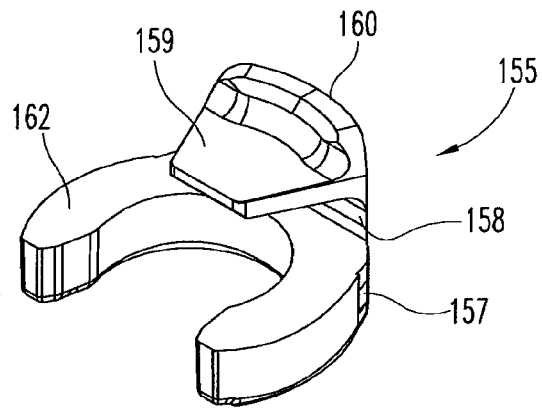
FIGS. 8a, 8b and 8c are respectively perspective, bottom perspective and top views of a syringe carriage shown separate from the other apparatus components.
Figure 8B:
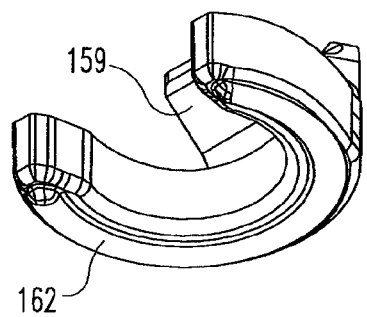
Figure 8C:
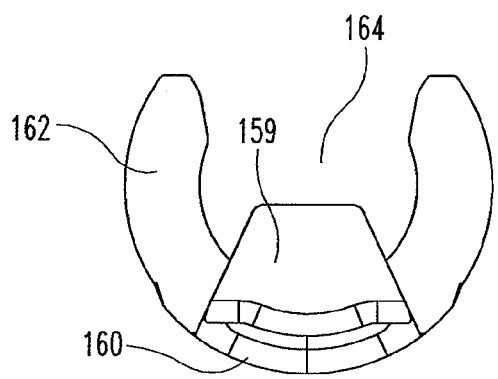
Figure 8D:
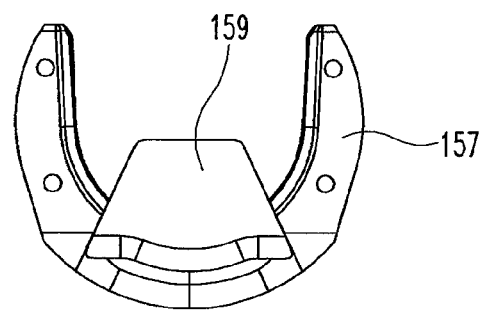
FIG. 8d is a top view similar to that of FIG. 8c but prior to the syringe carriage being overmolded.
Figure 9A:
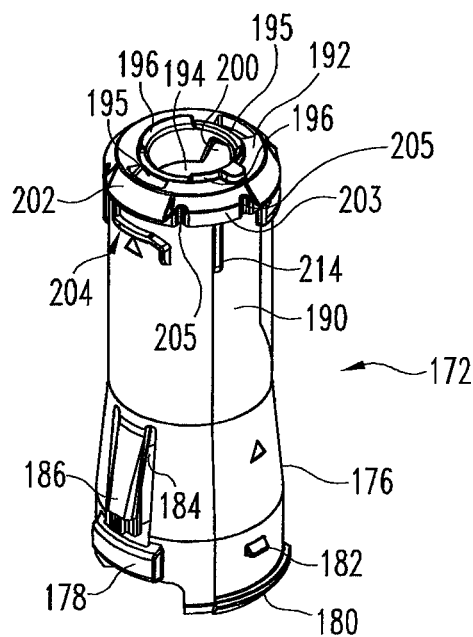
FIGS. 9a, 9b, 9c, 9d and 9e are respectively perspective, first side, second side, longitudinal cross-sectional, and bottom perspective views of an upper shuttle part shown separate from the other apparatus components.
Figure 9B:
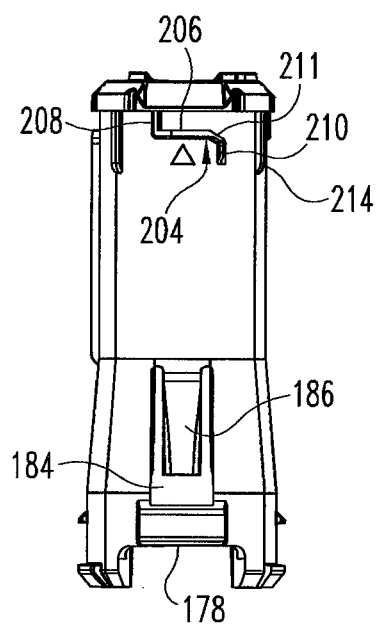
Figure 9C:
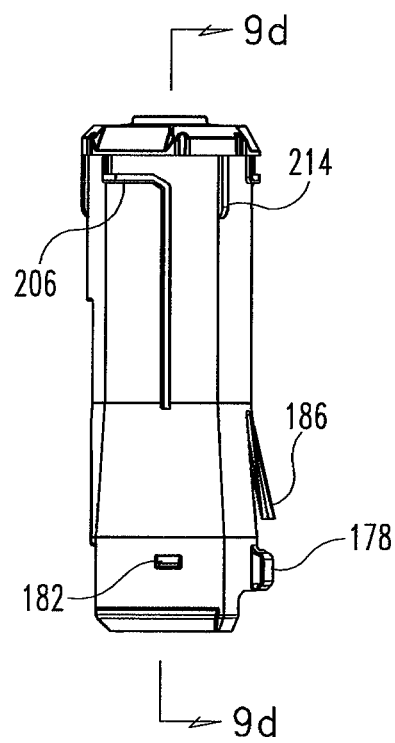
Figure 9D:
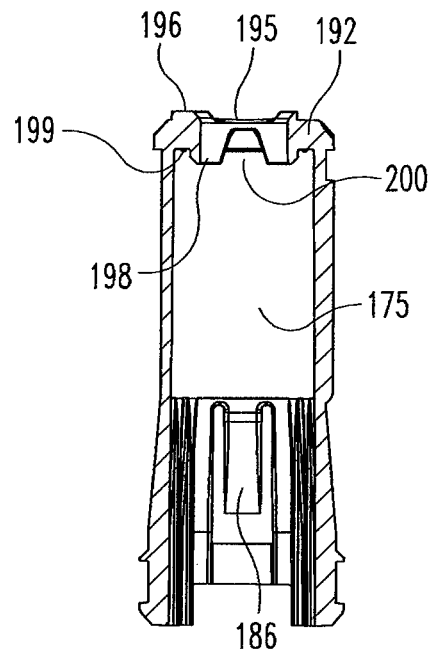
Figure 9E:
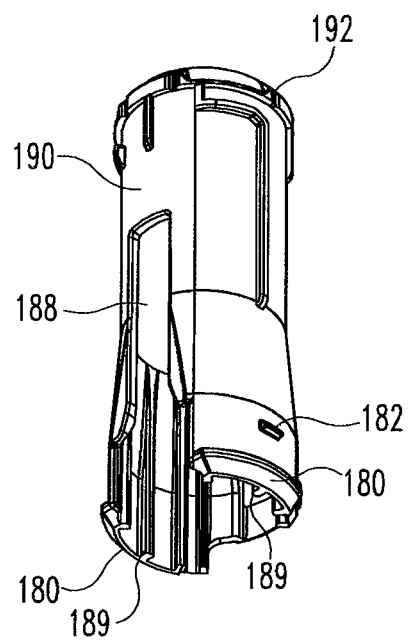

The housing 22 of the shown apparatus 20 also includes a baseplate 50, further shown in FIGS. 4a, 4b and 4c, and an upper body 26 that serves as the safety sleeve, further shown in FIGS. 5a, 5b, 5c and 5d. Baseplate 50 is made of the same material as housing main body 24 and includes a generally trilobular bottom portion 51 that is keyed to fit within the complementarily shaped-opening at the proximal end 32 of housing body 24 where it is fixedly secured during manufacture, such as via ultrasonic welding. A central aperture 52 of baseplate portion 51 through which a syringe needle moves out from and then back into the housing during use is ringed by a tube portion 54 that distally extends from portion 51. An interior surface 55 of tube portion 54, which starting at the tube distal end slopes inward as it extends proximally, includes a circumferential shoulder 56 that aids in centering the syringe. A set of three arcuate slots 58 are formed through portion 51 and are flanked by snaps 59 on the distal face of baseplate portion 51.

A syringe overcap 320, shown in FIG. 2, is made of plastic such as polypropylene SR549M, and includes a base 322 with a knurled periphery 323. A series or three arcuate cams 325 are in registry with slots 58 and include outwardly facing detents 326 that engage baseplate snaps 59 for a releasable interconnection. A tubular collar 328, upstanding from base 322, is adapted to engage a needle shielding assembly 330 that maintains the needle sterility and which is removed from the needle when the overcap is removed from housing 22.

The housing upper body 26 is a sleeve made of a plastic material, such as Lustran ABS 348 that is opaque. A manually grippable main body portion 62 transitions to a reduced diameter portion 64 that fits within the upper portion of housing main body 24. A circumferential groove 66 in the outer cylindrical periphery of sleeve portion 64 receives housing snap ring 36 during device assembly to allow rotational motion but to prevent axial motion between upper body 26 and main body 24. Opposed notches 68 are formed in the proximal edge of sleeve portion 64. One of the notches 68 accommodates the distal end of housing key 38 to limit the extent of locking sleeve rotation. An opening 70 through sleeve portion 64 forms a lock ledge 71 for shuttle capture. A raised indicator 73 formed on the outer periphery of body portion 62 provides a visual notice function in conjunction with lock and unlock icons shown at 76 in FIG. 1 provided on a label 75 adhered around the housing main body 24. Indicator 73 aligns with icons 76 when the sleeve 26 is rotationally disposed at end angular positions allowed by the abutment with key 38 of the sleeve stops defined by the notch 68.

The interior surface 78 of housing upper body 26 includes a set of three equally angularly spaced and inwardly projecting snap bumps 80 for engagement with the device button 25. A projecting, axially extending rib 82 formed on surface 78 fits within a button slot.

Button 25 is made of a sturdy yet suitably resilient material, such as Lustran ABS 348, and is further shown in FIGS. 6a, 6b, 6c, 6d and 6e. Button 25 includes an end disc 88 with a skirt 90 extending proximally from its outer periphery. End disc 88 has a distal face upon which a force can be directly applied by a user to selectively plunge the button to trigger the apparatus. A notch 92 formed in skirt 90 at its proximal end extends axially and forms a slot which receives rib 82 of housing body 26 so as to rotatably key together the button 25 and body 26. A set of three equally angularly spaced resilient fingers 94 each provided with a detent bump 95 on its radially inward face are provided at the base of skirt 90. Each finger 94 is adjacent to one of three equally angularly spaced fingers 97 with inwardly angled stops 98 also provided in skirt 90. Fingers 94 with bumps 95 cooperate with features on the shuttle to help rotationally locate button 25 on the shuttle, and fingers 97 with stops 98 cooperate with features on the shuttle to attach button 25 to the shuttle and help stage device operation.

Depending from the underside of disc 88 to a height above the proximal tips of fingers 94 and 97 is an activating element 100 of the button that is generally tube shaped. The interior surface of button element 100 at its proximal end is chamfered to form a camming surface 102. A pair of diametrically opposed notches 104 in the proximal end of element 100 serves as clearance slots.

Skirt 90 is formed with openings therethrough that define a multitude of resilient snaps or latches 106 that are used to secure the button 25 relative to housing upper body 26 after button plunging. Three such angularly spaced latches 106 are shown. Detents 107 formed in the outer periphery of skirt 90 proximally of each latch 106 facilitate manufacturing assembly.

As shown in FIG. 2, a medication-filled syringe, generally designated 110, is mounted within apparatus 20. Syringe 110 is shown as including a barrel 112, such as made of glass or other suitable material, with an injection needle 114 mounted at its proximal end which is in fluid communication with the medication contents of the syringe barrel and initially covered by a needle shielding assembly 330. The plunger mechanism of the syringe is formed in two parts by a plunger element, generally designated 116, and an elastomeric sealing member or piston 118 that seals the medication within barrel 112. The shown barrel 112, needle 114, needle shielding assembly 330 and piston 118 are of conventional design, but may be differently configured while still providing suitable functionality. For example, a flexible needle shield without a rigid needle shield may be possible, with suitable adaptations for the apparatus, such as to provide engagement of the flexible shield by the overcap.

Plunger element 116 is molded of a lightweight but sturdy and sufficiently resilient material, such as Delrin® 311DP from Dupont Engineering Polymers. As further shown in FIGS. 7a, 7b, 7c and 7d, plunger element 116 includes a proximal region 120 with a disc-shaped foot 121 at one end that serves to operationally abut sealing piston 118 during plunger advancement, and a disc-shaped flange 123 at the other end. A middle region 124 of the plunger element that extends axially upward from flange 123 includes an axially extending recess or cutaway 125 that further exposes an upper surface 126 of flange 123 which serves as a syringe carrier ledge. A disc-shaped flange 128 with a larger diameter than flange 123 is formed at the upper end of plunger middle region 124. A depending bar or outrigger 130 that during an injection directly engages a locking member to unlock the follower of the apparatus delay mechanism is formed on the outer radial periphery of flange 128. Unlocking bar 130 extends axially and proximally from flange 128 in spaced relationship with plunger middle region 124.

The distal region of plunger element 116 includes a pair of resilient prongs, generally designated 134, adapted to latchably engage a shuttle of the apparatus until released by the apparatus triggering mechanism for the shown embodiment. Each prong 134 includes an upstanding leg 136 that projects distally from a more central portion of flange 128 with an axially-aligned space or gap 137 between legs 136. At the distal end of its leg 136 each prong 134 includes a latch feature having a latching surface 138, an outward tip 139 at an outer extent of latching surface 138, and a ramp surface 141. Latching surface 138 extends generally radially outward from leg 136 and faces proximally. Latching surface 138 is formed with a slight undercut so as to slope slightly proximally from leg 136 to tip 139. Ramp surface 141 extends distally and at an angle inward from the tip 139 to form an outward facing ramp used in the inward camming of the prongs for release as described below. Each ramp surface 141, near its radially outer area and along a middle circumferential portion thereof, is interrupted by a locking protuberance 143 integrally formed therewith that projects distally toward button 25. Locking protuberance 143 extends upward the same extent as ramp surface 141 such that the upward tips of the locking protuberances 143 are disposed at the same height as the upward tips of the ramp surfaces 141. The upward tips of locking protuberances 143 are disposed radially outward of the upward tips of the ramp surfaces 141. The radially outwardly facing surfaces 146 of the upward tips of locking protuberances 143 are rounded to facilitate insertion through spring 149 during apparatus assembly.

Locking protuberance 143 and ramp surface 141 are in spaced relationship in that they define a radial space therebetween. A V-shaped opening 145 that the radial space forms between ramp surface 141 and the inward face of locking protuberance 143 is shaped and sized to receive the proximal end of button element 100.

An axially extending boss 147 formed on each leg 136 is provided to aid in centering the drive coil spring 149 shown in FIG. 2. The proximal end of spring 149, as centered by dogs 150 on flange 128, seats and acts against flange 128, and the distal end of spring 149 acts against the shuttle.

An overmolded syringe carrier further shown in FIGS. 8a, 8b, 8c and 8d is generally designated 155 and fits to a keyed flange 111 of syringe barrel 112 to be rotatably fixed together. Syringe carrier 155 includes a base formed of a rigid material, such as DCL4036 20% carbon filled polycarbonate, which base includes a generally C-shaped section 157 from which upwardly projects a support 158 with a radially inwardly protruding clip 159. A protrusion 160 is formed in the top of clip 159 and is used to facilitate the overmolding process. A softer overmolding 162 that fully covers the legs of base section 157 provides a cushioning for the glass syringe held by the carrier to reduce the likelihood of breakage. A suitable overmolding is made of an injection moldable thermoplastic elastomer. When apparatus 20 is fully assembled, syringe barrel 112 snugly fits within central opening 164 with syringe flange 111 captured axially between overmolding 162 and the underside of clip 159, and with the underside of the tip region of clip 159 facing for direct supportive engagement the upper surface 126 of plunger flange 123. This supportive engagement of the syringe carrier clip 159 by surface 126 prevents the syringe 110 held within carrier 155 from moving outward of the housing 22 before apparatus use.

The delay mechanism of apparatus 20 includes a shuttle, generally designated 170, a follower 250 that releasably latches with the shuttle 170, and a dual functioning biasing member 290 acting between the shuttle and the follower. In the shown embodiment, shuttle 170 is formed of an upper shuttle 172 and a lower shuttle 174 further shown in FIGS. 9a, 9b, 9c, 9d and 9e and FIGS. 10a, 10b, 10c, 10d and 10e, respectively. Shuttle parts 172 and 174 are fixedly connected during manufacturing assembly, such as with the described snap fit or other suitable connection manner, to together serve as the shuttle. The multi-piece construction facilitates molding and assembly of the shuttle, as well as the assembly of the apparatus components within the interior hollow 175 of the shuttle. One suitable material for shuttle part 172 is a plastic such as EXL1992T Polycarbonate alloy that is transparent, and one suitable material for shuttle part 174 is a polycarbonate such as Makrolon 2458 that is transparent.

The bottom portion 176 of upper shuttle 172 includes a protruding alignment block or key 178 that closely fits within a notch 222 formed in the distal end 223 of the body 220 of lower shuttle 174. During manufacturing assembly of the mating shuttle parts, radially protruding and partially circumferentially extending lips 180 provided on opposite sides of upper shuttle 172 snap lock over ledges 225 defined by windows 226 formed in lower shuttle 174. A pair of keys 182 projecting from the periphery of upper shuttle 172, one of each key 182 above each lip 180, fits into smaller notches 228 formed in the distal end 223 of shuttle body 220. The fitting of keys 182 within notches 228 and alignment block 178 within notch 222 rotatably fixes the shuttle parts together when connected.

The bottom portion 176 of upper shuttle 172 above block 178 includes an opening 184 from which a locking flexure 186 outwardly extends at an angle. Flexure 186 cooperates with the lock ledge 71 of the housing to secure the shuttle in a retracted position after use. On the side of shuttle 172 opposite of opening 184, an opening or slot 188 extending to the bottom of the upper shuttle is provided which accommodates plunger outrigger 130. Ribs 189 formed in the inner surface of bottom portion 176 serve as stops for abutment by syringe flange 111 to limit distal movement of the syringe 110 during assembly.

The upper portion of upper shuttle 172 is a tubular, cylindrical body 190 with an overhanging cap portion 192. A central aperture 194 through cap portion 192 allows passage of the latching portion of plunger prongs 134. A pair of dogs 196 that project distally from the top surface of cap portion 192 are diametrically opposed around aperture 194 and help guide activating element 100 of button 25 into aperture 194 during use. The prong-engaging surfaces 195 between dogs 196 include a ramping upward surface adjacent to aperture 194 that is complementary to the undercut of latching surfaces 138 to provide a more secure but releasable connection therebetween. A collar 198 depending from the underside 199 of cap portion 192 within hollow 175 centers the distal end of spring 149 that acts directly against underside 199. Two opposing cut outs 200 in collar 198 allow passage of locking protrusions 143 of prongs 134 and aid assembly by presenting a ramp surface that deflects the prongs inward during assembly.

The outer radial periphery of cap portion 192 includes three beveled sections 202 and three land sections 203 in alternating arrangement around the shuttle circumference. The angular ends of each land section 203 are defined by grooves or indents 205. Land sections 203 are designed to have detents 95 of button fingers 94 slide therealong during button rotation. Indents 205 cooperate with detents 95 to aid in keeping the button in one of two preferred angular or rotational positions relative to the shuttle 170, but which detent connections can be readily overcome when the button is moved between such positions by manual rotation of the sleeve 26. The interaction between indents 205 and detents 95 also provides a tactile and audible indication of when the button rotation has reached an end point.

Three stop ribs, generally designated 204, project from the periphery of shuttle body 190 proximally of the three cap beveled sections 202. Each stop rib includes a circumferentially extending segment 206, an upstanding axially extending segment 208 at one end of segment 206, and a depending axially extending segment 210 with an angled lead-in 211 at the other end of segment 206. Three axially extending stop ribs 214 are provided proximally of the three land sections 203.

During manufacturing assembly, button 25 is mounted to shuttle 170 by moving the parts axially together such that button fingers 97 with stops 98 slide and snap fit over cap beveled sections 202, at which point distal removal of the button is resisted by stops 98 abutting the overhanging lip of the beveled sections 202 of cap portion 192. When button 25 is so mounted, rib segments 206 serve as axial stops for button stops 98 to abut and thereby frustrate manual button plunging when the button is not in an unlocked state. Rib segments 208 work with stops 98 to further prevent button 25 from being rotated in the wrong direction from a locked state, and stop ribs 214 prevent button 25 from being rotated too far during unlocking. Rib segments 210 and stop ribs 214 guide the downward travel of the button during its plunging, and the longer rib segment 210 shown in FIG. 9c serves as an abutment for a stop 98 to prevent manual relocking of the sleeve 26 during fluid delivery.

Lower shuttle 174 is generally tubular with a cylindrical body 220 that steps down via a substantially annular, radially aligned flange 221 to a reduced diameter, cylindrical proximal region 230 that fits within follower 250. Flange 221 is interrupted by an upstanding rib region 247. Flange 221 serves as the support that directly engages the syringe carrier 155 for effectively engaging and carrying the syringe upward to withdraw the syringe needle after injection. A bar 238 that extends distally from distal end 223 is used to rotatably lock housing sleeve 26 after an injection by fitting within a notch 68. At its proximal end, shuttle 174 includes an annular lip 233 that extends radially inward to define the opening through which extends syringe barrel 112. An annular recess provided around the end of proximal region 230 outward of lip 233 forms a shoulder 231 that seats and centers the biasing member 290 described below that acts on the shuttle. An axially extending groove 232 in lower shuttle body 220 receives housing key 38 to rotatably fix shuttle 170 with housing 22 along the entire axial travel of the shuttle therein.

The shuttle includes at least one latching element for releasably engaging the follower of the delay mechanism. The latching element is shown provided as a set of tabs 234 and 236 that are angularly spaced around and radially outwardly project from proximal region 230 near its proximal end. Tabs 234 and 236 are shown as differently sized, block-shaped projections that serve as latching hooks to engage the follower.

Figure 10A:
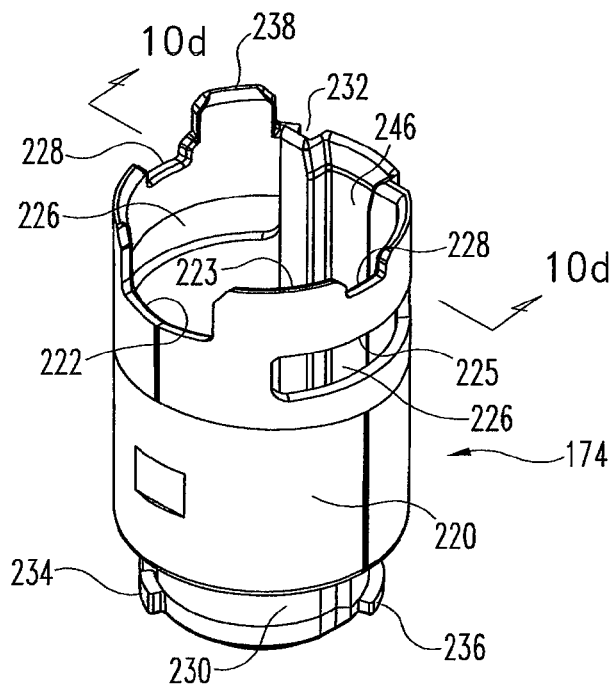
FIGS. 10a, 10b, 10c, 10d and 10e are respectively perspective, first side, second side, longitudinal cross-sectional, and bottom views of a lower shuttle part shown separate from the other apparatus components.
Figure 10B:
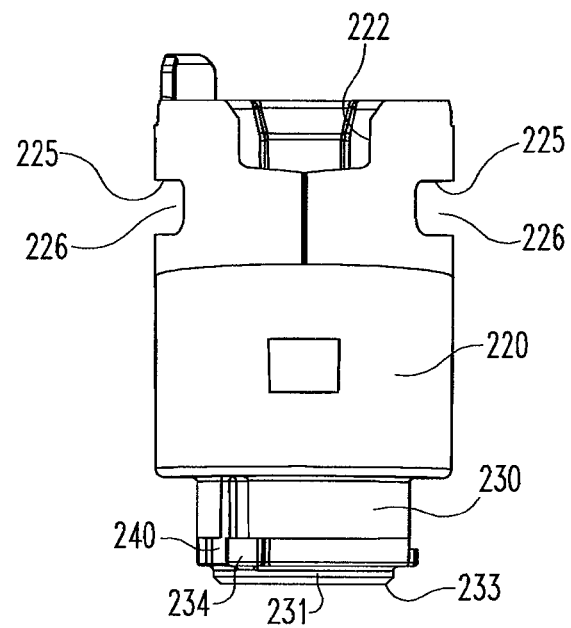
Figure 10C:
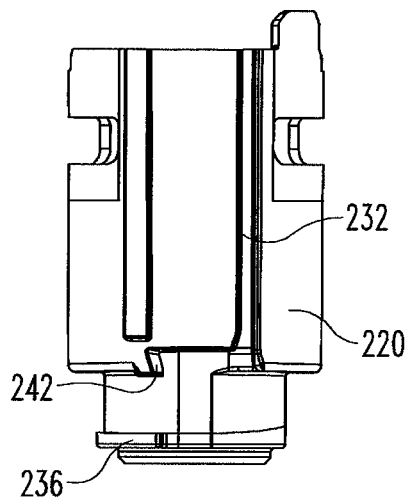
Figure 10D:
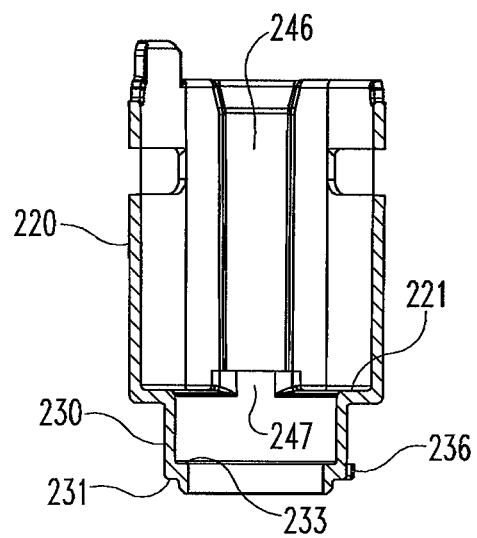
Figure 10E:
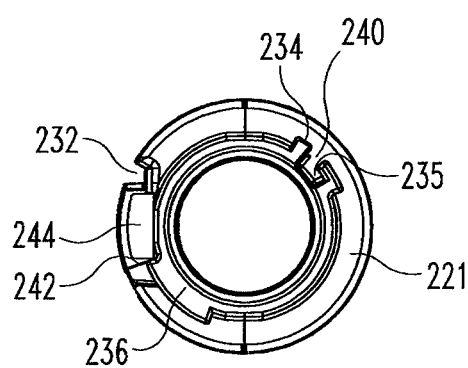
Figure 11A:
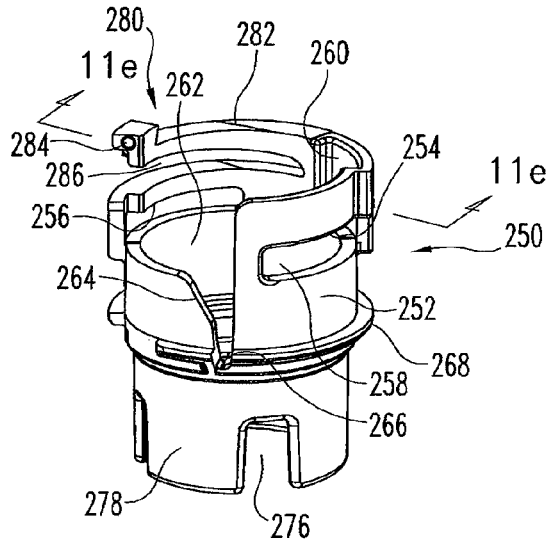
FIGS. 11a, 11b, 11c, 11d and 11e are respectively first perspective, first side, second perspective, second side and longitudinal cross-sectional views of a follower shown separate from the other apparatus components.
Figure 11B:
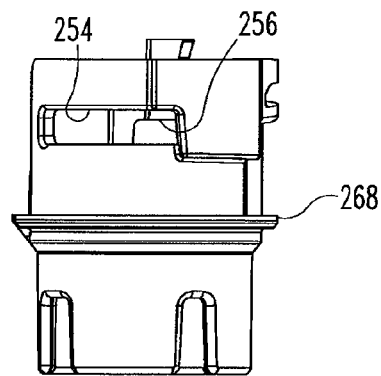
Figure 11C:
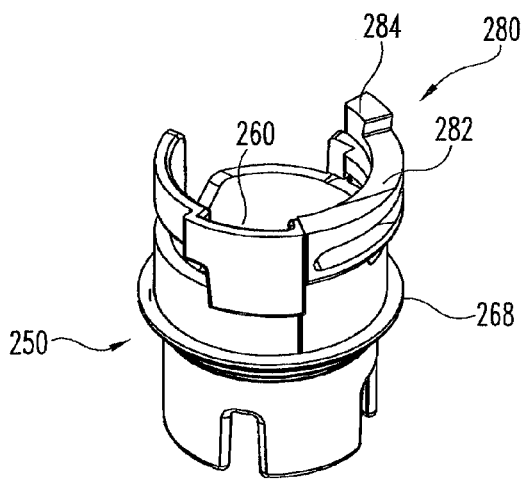
Figure 11D:
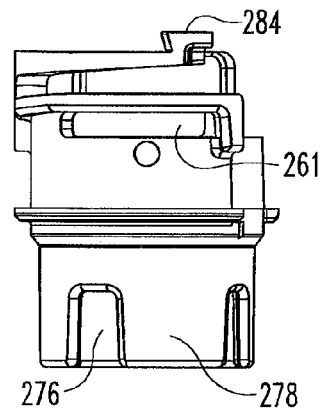
Figure 11E:
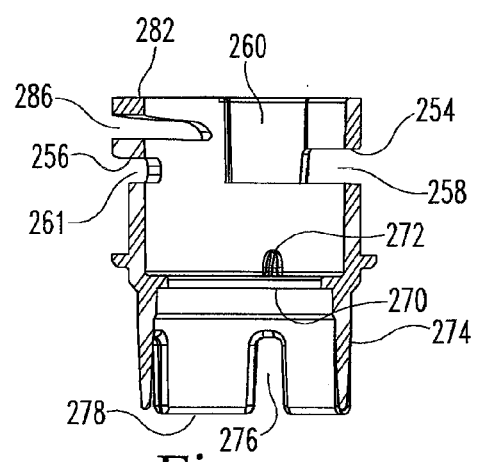

An axially oriented notch 240 that opens radially outward is formed through tab 234 and into shoulder 231. Notch 240 is sized and configured to receive an upper projection 294 of the biasing member. As shown in FIG. 10e, notch 240 includes a circumferential jog at its inward depth that results in tab 234 providing a pocket 235 for radially retaining the biasing member upper projection.

At the proximal end of lower shuttle body 220 on its outer periphery, an angled, locking latch surface 242 is formed therein. Latch surface 242 is disposed proximally of and angularly adjacent to an opening 244 formed in the upward protruding rib region 247. Opening 244 is disposed in line with an axially extending channel 246 formed in the interior surface of lower shuttle body 220 along its entire height. The edges of rib region 247 defining opening 244 are sloped to help lead outrigger 130 into the opening. Channel 246 accommodates plunger outrigger 130 to loosely rotatably key shuttle 170 and plunger element 116 while allowing axial motion of the plunger element 116 relative to the shuttle such that the proximal tip of outrigger 130 can project through opening 244 to unlock the locking mechanism described below.

The delay mechanism follower 250 is further shown in FIGS. 11a, 11b, 11c, 11d and 11e. Follower 250 is formed of a rigid yet sufficiently resilient material to integrally provide the locking member feature. One suitable material for the shown follower 250 is Delrin® 311DP. Follower 250 includes an upper portion 252 that fits concentrically around shuttle proximal region 230. Two partially circumferentially extending ledges 254 and 256 are formed in follower portion 252 and serve as latching elements that engage shuttle latching tabs 234 and 236. Ledge 254 is formed by a window 258 through follower portion 252 and opens at one angular end to an axially extending channel 260 formed in the interior surface of follower portion 252. Ledge 256 in part opens to window 261 and at one angular end opens to an opening 262 in follower portion 252. Channel 260 and opening 262 allow axial movement of tabs 234 and 236 therein for manufacturing assembly and for shuttle release relative to the follower during apparatus use. Opening 262 tapers at 264 to a slot-shaped portion 266 adapted to closely receive a radial projection 296 of the biasing member.

Near the base of follower portion 252, a flange 268 that extends around the majority of the circumference projects radially outward from follow portion 252. Flange 268 snaps past housing snaps 44 during apparatus assembly. The interior surface of follower portion 252 includes an inwardly projecting ring 270 provided with three equally angularly spaced ribs 272 on its upper face. Ring 270 defines an opening through which the syringe barrel extends and provides a seat for the biasing member that is centered by ribs 272

A sleeve shaped lower portion 274 of follower 250 depends from follower portion 252 and has a lesser diameter. Four slots 276 in the proximal edge of portion 274 define four damping fins 278 of the follower.

A locking member for follower 250 to limit its rotation relative to the shuttle 170 is integrally formed with follower 250. In alternate embodiments, differently configured locking members, including being a separate piece or being formed with the shuttle, may be employed. The locking member is generally designated 280 and is formed as a flexure arm 282 with an upwardly extending latch 284 at its end. Flexure arm 282 extends in a generally circumferential direction from follower upper portion 252. As flexure arm 282 occupies a similar annular space as follower portion 252, and because arm 282 is designed to be bent axially to cause latch 284 to be moved axially relative to the shuttle in order to unlock the follower for rotation, an axial space 286 between arm 282 and the area of the follower portion above window 261 is provided to accommodate arm bending. Such space would not be required if, for example, the latch was unlocked via a radial movement thereof.

The dual functionality of biasing member 290 results from it providing a torsional force and an axial force during use, both of which forces act directly between follower 250 and shuttle 170. For the configuration shown in apparatus 20, biasing member 290 functions as both a torsion spring and a compression spring, and can be made as a single component that is readily handled during manufacturing assembly. The torsional force and axial force result from a release of a torsional preloading and an axial preloading of the biasing member 290, which preloading has been accomplished during the manufacturing assembly of apparatus 20.

Biasing member 290 is shown as a cylindrical spring formed of a helically coiled wire 292. One suitable such spring is made of 302 stainless steel with a wire diameter of 0.024 inch. Spring 290 is selected to provide suitable torsional and axial forces within the available space, and the selection is dependent upon the device operation, such as the delay required, and the design of the cooperating components, such as the damping compound and follower and grease cup configurations. Other designs of biasing members, such as a metal or plastic flexure configured to perform the dual functions, may be substituted for the single metal coil spring shown.

Figure 12A:
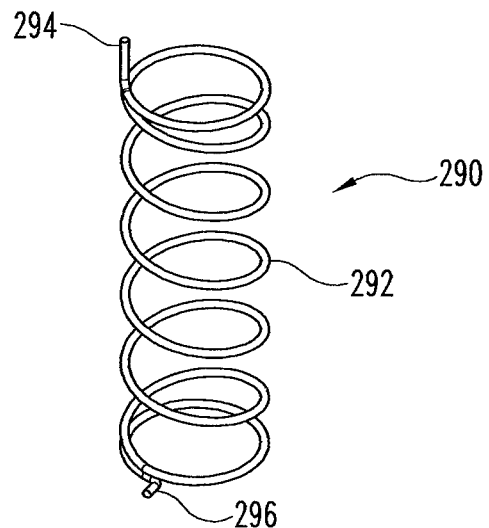
FIGS. 12a, 12b and 12c are respectively perspective, side and top views of a dual functioning biasing member in an unstressed or not preloaded state shown separate from the other apparatus components.
Figure 12B:
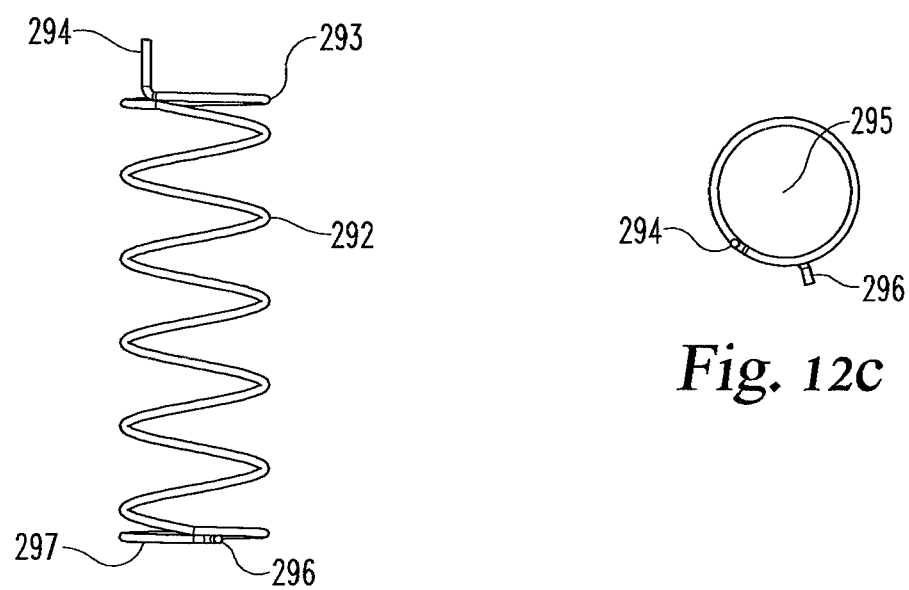
Figure 12C:
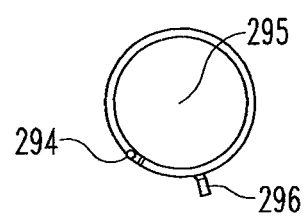
Figure 13A:
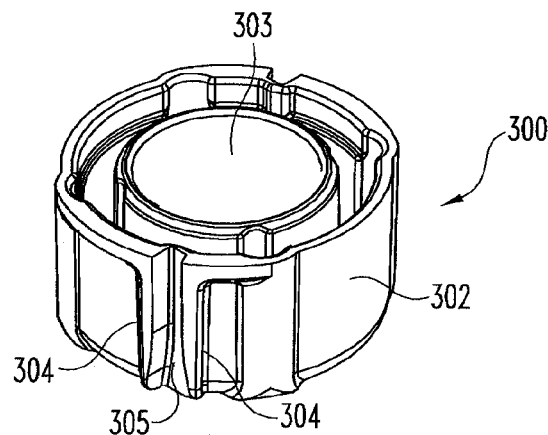
FIGS. 13a, 13b, 13c and 13d are respectively perspective, side, longitudinal cross-sectional and top views of a grease collar shown separate from the other apparatus components.
Figure 13B:
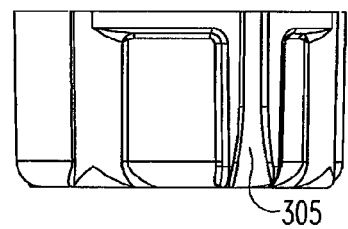
Figure 13C:
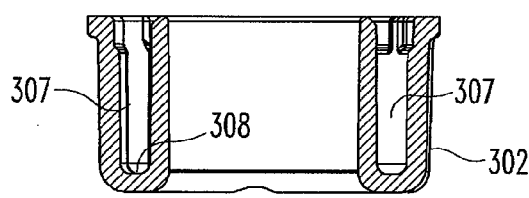
Figure 13D:
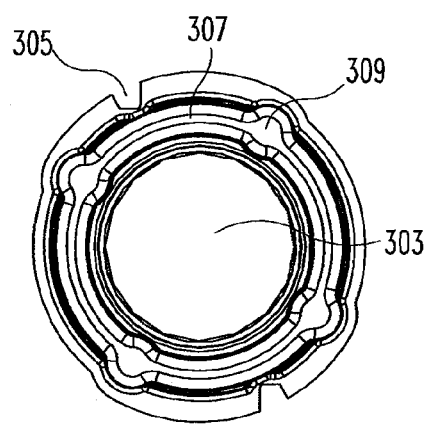

The internal opening 295 of spring 290 freely receives lower shuttle proximal region 230, while the outer diameter of spring 290 freely fits within follower upper portion 252. The distal end coil 293 of wire 292 which abuts the shuttle shoulder 231 terminates with a protruding end or tip 294 that projects distally. Tip 294 is disposed within the cross-sectional area of the cylindrical coil as shown in FIG. 12c. Tip 294 is sized and shaped to fit within shuttle pocket 235 to engage shuttle 170. The proximal end coil 297 of wire 292 which abuts the follower ring 270 terminates with a radially outwardly protruding tip 296. Tip 296 extends beyond the cross-sectional area of the cylindrical coil. Tip 296 is sized and shaped to closely fit within opening portion 266 to engage follower 250.

During manufacturing assembly of apparatus 20, with spring 290 arranged so that tips 294 and 296 respectively fit within pocket 235 and opening 266 of the spaced follower 250 and lower shuttle 174, spring 290 is preloaded both axially and torsionally between follower 250 and shuttle lower portion 174 as the follower and shuttle lower portion are brought together axially and rotated so as to be latched, via the interaction of ledges 254, 256 and tabs 234, 236, and then so locked, via the interaction of locking member 280 and shuttle surface 242.

A grease cup or collar, generally designated 300, is further shown in FIGS. 13a, 13b, 13c and 13d. Cup 300 provides a support surface for the damping fluid as the follower 250 rotates relative to that support surface. In an alternate embodiment, the support surface can be otherwise provided, such as being integrally formed with the housing body. Cup 300 is made from a plastic material, such as ABS TR-558A1 from LG Chemical Ltd, that is transparent. Cup 300 includes an annular body 302 that has a generally cylindrical outer periphery, and a round central aperture 303 through which fits the syringe barrel. Cup 300 is axially supported within housing 22 by ledges 40. Ribs 304 define a keying slot 305 on the outer periphery. Two slots 305 are shown, but only one is needed to fit over the housing spline 42 that rotatably fixes cup 300 and housing 22, and the other slot makes initial orientation less critical during assembly as well as typically allows passage over key 38 during assembly. Cup body 302 includes a generally U-shaped wall portion 308 that defines an annular hollow or channel 307. Enlarged areas 309 that open into the top of hollow 307 are so sized to better accommodate the nozzles by which the damping compound is inserted into the hollow 307.

A damping compound or fluid 315, such as a silicone grease thickened with Teflon available from Nye Lubricants as Nye fluorocarbon gel 880, fills annular hollow 307. Follower fins 278 fit within hollow 307 such that compound 315 is disposed both radially inward and outward of such fins 278, as well as between adjacent fins 278 and as a film between the fin undersides and the base of the follower wall, resulting in a damping or delay effect as the follower fins 278 try to rotate relative to the U-shaped interior surface of wall portion 308 with the viscous damping fluid providing a resistance to this rotation during operation. Other compounds with different properties may be selected by one of skill in the art in view of the delay selected by the manufacturer to be provided by the delay mechanism, and in view of modifications that may be made by the skilled artisan to the placement of the compound as well as other aspects of the delay mechanism, such as the spring-generated torsional force and the size and shape of the follower and the grease collar.

The construction of apparatus 20 will be further understood in view of a description of its operation. With the apparatus initially configured in a locked state as shown in FIGS. 1 and 2, the apparatus cannot be triggered. If a user applies a plunging force on button 25, the button stops 98 axially abut shuttle rib segments 206. Furthermore, due to button activating element 100 extending within V-shaped opening 145 but with clearance slots 104 being rotationally out of alignment from locking protuberances 143, the protuberances 143 will abut the outer periphery of element 100 and prevent inward movement of prongs 134 sufficient for disengagement from the shuttle.

Figure 14:
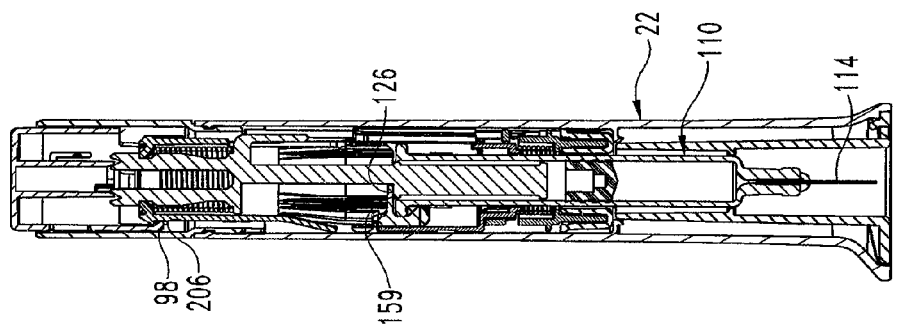

The syringe overcap 320 is then manually removed by the user overcoming the engagement of overcap detents 326 with snaps 59 and pulling the overcap proximally off of the housing to also remove the needle shielding assembly 330. This overcap removal is facilitated by the user twisting the overcap relative to the housing, which twisting, due to the camming effect of cams 325 against plate 51, shifts the overcap proximally. The engagement of the syringe carrier clip 159 with plunger flange surface 126 limits proximal motion of syringe 110. After overcap removal, apparatus 20 is arranged as shown in FIG. 14.

Figure 15:
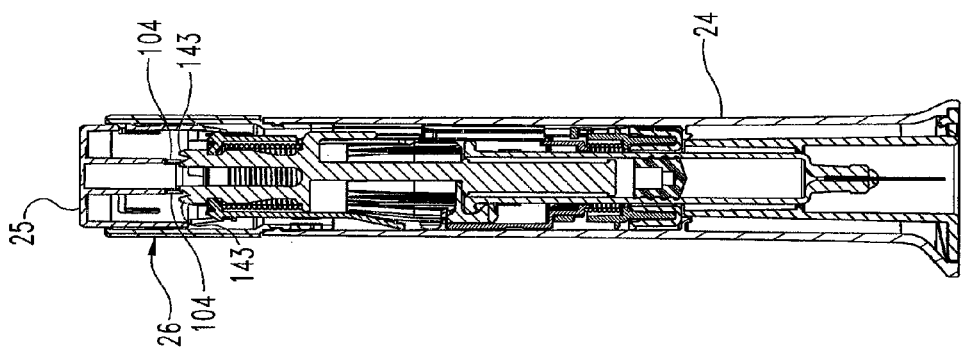

To allow for an injection, the locking or safety that prevents triggering needs to be unlocked. This unlocking can be done before or after the apparatus 20 is oriented at the injection site. The user can grip and manually rotate locking sleeve 26 relative to the housing main body 24 until the alignment indicator 73 is in registry with the unlock icon of icons 76, at which the edge of sleeve notch 68 abuts housing key 38. This rotation of sleeve 26 rotates button 25 due to the keyed connection therebetween. Besides the visible icon, the unlocked registration or state also will be indicated by the button finger detents 95 snapping into the indents 205 at the opposite ends of the land sections 203 at which the button detents were initially located in FIG. 14. At this point, button stops 98 have been moved angularly clear of shuttle rib segments 206, and clearance slots 104 are now rotationally aligned with protuberances 143, and apparatus 20 is arranged as shown in FIG. 15 and prepared for an injection.

Figure 16:
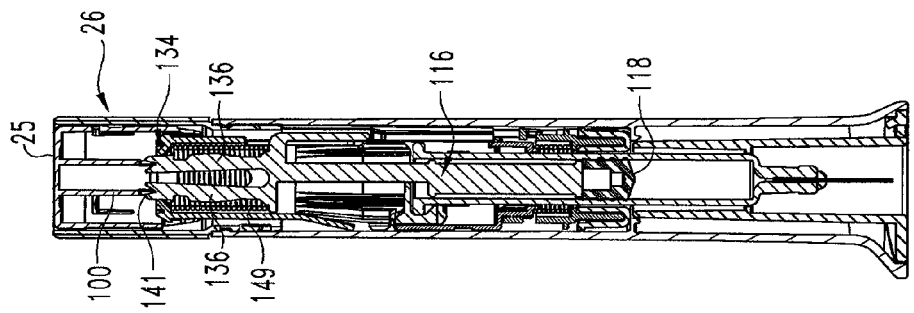
FIGS. 14-19 are longitudinal cross-sectional views of the automatic injection apparatus of FIG. 1 at subsequent stages of its operation.

In this prepared state, and with the apparatus positioned at an injection site, when a user applies a plunging or downforce on button 25, button 25 starts to move into housing sleeve 26 as activating element 100 engages prong ramp surfaces 141. As button 25 moves further, prong legs 136 bend inward, reducing gap 137, due to the camming inward of the ramp surfaces by the button element 100. Locking protuberances 143 fit through clearance slots 104 so as to not prevent this prong inward motion. When prongs 134 have been bent inward sufficiently to disengage latching surfaces 138 from shuttle surfaces 195, at which point the plunger prongs can fit through the shuttle opening 194 as shown in FIG. 16, the drive spring 149 directly biases the plunger element 116 downward to drive it and thereby piston 118 proximally, which driven motion shifts syringe barrel 112 proximally relative to the shuttle and the housing 22 to cause the tip of needle 114 to project beyond housing proximal end for penetrating a user's skin, and then forces the medication contents of the syringe through that needle for an injection. In FIG. 16, the button 25 is shown at the end of its plunging, at which arrangement sleeve rib 82 reaches the end of button slot 92, and button latches 106 have snap fit under sleeve snap bumps 80 to hold the button in its plunged condition relative to the housing, and with button end disc 88 flush with the top edge of sleeve 26 so as to visually indicate apparatus use. In FIG. 16, the plunger element is shown unlatched from the shuttle but before the spring 149 has largely uncoiled to drive the plunger element downward.

Figure 17:
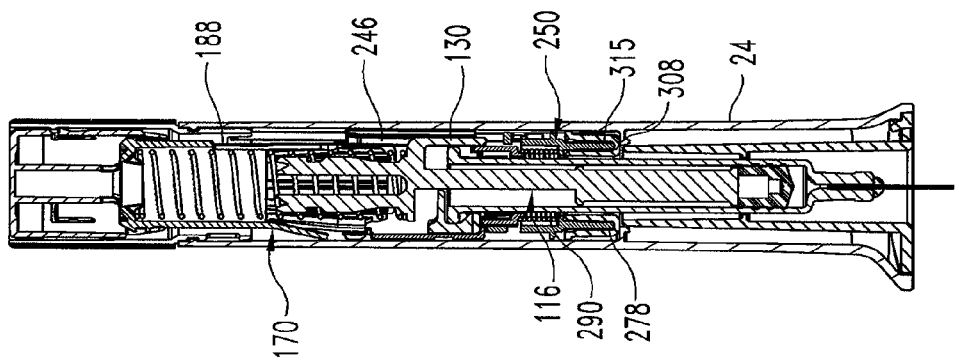

As plunger element 116 moves proximally during medication injection, the outrigger 130 of the plunger element, as shown in FIG. 17, slides within shuttle slot 188 and then channel 246 until the proximal tip of outrigger 130 enters opening 244 and abuts and unlocks locking member 280. In particular, the outrigger 130 abuts an upper face of latch 284 and shifts latch 284 axially, by bending flexure 282 to close the gap 286, which axially shifting unlatches latch 284 from shuttle latching surface 242 so as to unlock the follower 250 for rotation. This unlocking typically will be designed to occur shortly before the end of proximal travel of the plunger mechanism.

Figure 18:
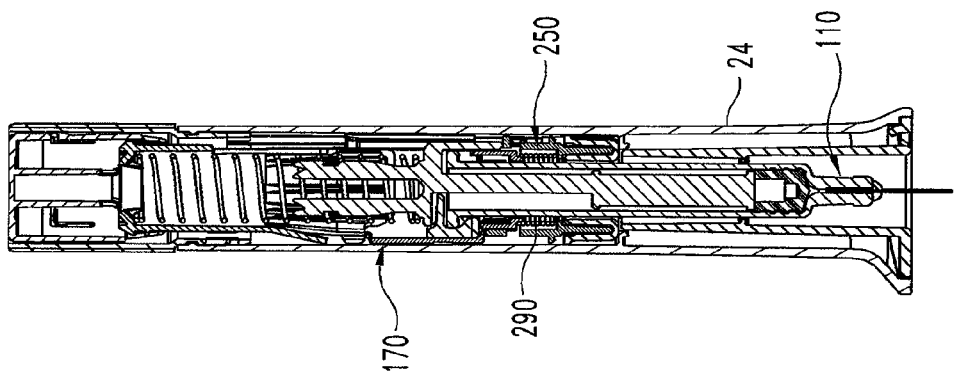

When locking member 280 is so unlocked or released, the follower 250, as urged by the torsional preloading of biasing member 290, rotates within the housing 24 and around the rotatably fixed shuttle 170. The viscous damping compound 315 between the follower fins 278 and cup wall portion 308 dampens or offers a resisting force to this follower rotation, which resistance results in a passage of time before shuttle unlatching, during which time remaining medication can be properly expelled from the syringe through the needle. Rotation of follower 250 about shuttle 170 is driven by spring 290 until follower opening 262 and channel 260 align with shuttle tabs 236 and 234, respectively. In this arrangement, at which apparatus 20 is shown in FIG. 18, tabs 234 and 236 are clear of ledges 254 and 256 such that shuttle 170 and follower 250 are unlatched.

Figure 19:
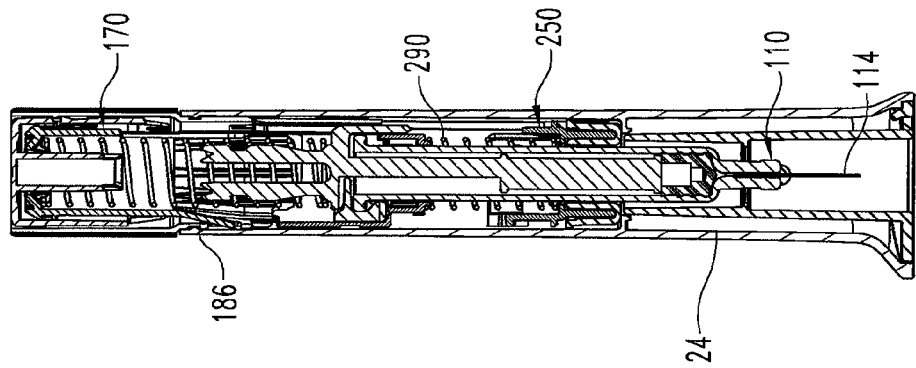

When shuttle 170 and follower 250 are so unlatched, the shuttle 170, as urged by the compressive preloading of biasing member 290, translates distally within the housing 24 until distal end 223 of lower shuttle 174 meets the proximal end 69 of body 26. As shuttle 170 is retracted, the needled syringe 110 is carried by the shuttle distally so as to retract the proximal tip of the injection needle 114 to a protected position within the housing 24. The shuttle is held in this retracted position by the axial force of the biasing member 290 and is locked in this retracted position by the snap fitting of shuttle locking flexure 186 within opening 70 against ledge 71. Attempts by the user to rotate sleeve 26 relative to housing 24 is frustrated by the presence of bar 238 within a notch 68. At this point, the apparatus is configured as in FIG. 19, and the user then can dispose or otherwise handle the apparatus in the normal course.

Apparatus 20 is designed to facilitate its manufacturing assembly. For example, a subassembly of lower shuttle 174, spring 290, follower 250, and damping collar 300 with damping compound 315 can be snap fit into a housing subassembly of main body 24 and baseplate 50. Another assembly process can involve placing a syringe 100 in alignment with a subassembly of upper shuttle 172, drive spring 149, plunger element 116, button 25 and sleeve 26, snap assembling syringe carrier 155 to the syringe and plunger element, assembling this entire subassembly to the previously assembled lower shuttle assembly and housing, applying a label to the housing, and then securing the overcap 320 to the housing baseplate 50 in engagement with a previously assembled needle shielding assembly 330.

While this invention has been shown and described as having preferred designs, the present invention may be modified within the spirit and scope of this disclosure. For example, differently configured releasable locking members may be used to keep the syringe and follower rotationally fixed despite the torsional force applied by the biasing member. Furthermore, the shuttle and the associated delay mechanism can be used in apparatuses with different other components, such as alternate trigger locking devices, just as the shown trigger locking device can be used with differently configured automatic syringe moving mechanisms. Still further, the dual functioning biasing member may be configured to work with differently configured components of a delay mechanism, such as a delay mechanism in which the shuttle and follower still have a fluid dampened relative rotation upon unlocking, but where the follower and shuttle do not unlatch after follower rotation but rather move together axially when the follower instead unlatches from the housing, and the dual functioning biasing member acts not directly between the follower and shuttle in such delay mechanism but rather acts between the follower and housing. This application is therefore intended to cover any variations, uses or adaptations of the invention using its general principles. Further, this application is intended to cover such departures from the present disclosure as come within known or customary practice in the art to which this invention pertains.

We claim:

1. In an automatic injection apparatus having a housing, a needled syringe with a plunger, and at least one biasing element for moving the needled syringe in a first direction within the housing to extend the needle of the syringe beyond the housing and to advance the plunger to force syringe contents through the needle for an injection, a delay mechanism comprising:

a shuttle for the syringe, said shuttle including a first latching element;

a follower including a second latching element, said second latching element for cooperating with said first latching element to limit motion of said shuttle relative to said follower in a second direction opposite the first direction;

a locking member movable within said housing from a locking position to a release position by engagement with the syringe plunger during an injection, said locking member, when in said locking position, preventing rotation of said follower relative to said shuttle, said locking member, when in said release position, allowing rotation of said follower relative to said shuttle;

a damping compound between said follower and a supporting surface to dampen rotation of said follower relative to said shuttle;

a dual functioning biasing member having a torsional preloading and an axial preloading, said dual functioning biasing member acting between said shuttle and said follower to provide both a torsional force urging said follower to rotate relative to said shuttle and an axial force urging said shuttle away from said follower;

whereby when said locking member moves to said release position during an injection, said dual functioning biasing member first forces said follower to rotate relative to said shuttle from a latching position, at which said first and second latching elements cooperate, to an unlatching position, at which said second latching element is disengaged from said first latching element, and then said dual functioning biasing member forces said shuttle axially relative to said follower to move said shuttle for retracting the syringe needle into the housing after injection.

2. The delay mechanism of claim 1 wherein said dual functioning biasing member comprises a coiled spring having first and second ends that directly engage said follower and said shuttle respectively.

3. The delay mechanism of claim 2 wherein said coiled spring first end includes a radially outwardly extending tip that fits within a complementarily shaped recess formed by an opening through a body of said follower.

4. The delay mechanism of claim 2 wherein said coiled spring second end includes an axially extending tip that fits within a complementarily shaped recess formed in said shuttle.

5. The delay mechanism of claim 4 wherein said recess formed in said shuttle is formed in a radially projecting tab that comprises said first latching element.

6. The delay mechanism of claim 1 wherein said supporting surface comprises a surface of a collar rotatably fixed relative to the apparatus housing.

7. The delay mechanism of claim 1 wherein said locking member comprises at least one flexure integrally formed with said follower and axially movable relative to the shuttle from a locking position to a release position by engagement with an outrigger of the syringe plunger during an injection.

8. The delay mechanism of claim 1 wherein said shuttle comprises a support against which acts the biasing element that moves the needled syringe in the first direction and advances the plunger, whereby biasing of the shuttle for retracting the needle is not resisted by the biasing element that advances the plunger.

* * * * *